United States Patent [19]

Harris et al.

[11] Patent Number: 4,806,636

[45] Date of Patent: Feb. 21, 1989

[54] **HETEROPOLYSACCHARIDE PRODUCED BY *ENTEROBACTER SAKAZAKII***

[75] Inventors: L. Scott Harris; Patrick J. Oriel, both of Midland, Mich.

[73] Assignee: The Dow Chemical Company, Midland, Mich.

[21] Appl. No.: 714,147

[22] Filed: Mar. 20, 1985

[51] Int. Cl.$^4$ .................... C08B 37/00; C12P 19/04; C12N 1/20; C12R 1/01
[52] U.S. Cl. ............................ 536/123; 435/101; 435/252.1; 435/822
[58] Field of Search ............ 435/101, 104, 822, 253; 536/123; 252/9, 11

[56] References Cited

U.S. PATENT DOCUMENTS

| | | | |
|---|---|---|---|
| 3,305,016 | 2/1967 | Lindblom | 166/9 |
| 3,326,733 | 6/1967 | Colegrove | 149/20 |
| 3,655,579 | 4/1972 | Crothy et al. | 252/316 |
| 3,933,788 | 1/1976 | Kang et al. | 260/209 |
| 4,233,438 | 11/1980 | Myers et al. | 536/123 |
| 4,286,059 | 9/1981 | Suk Kang et al. | 435/101 |
| 4,329,448 | 5/1982 | Cox et al. | 536/123 |
| 4,350,769 | 9/1982 | Kang et al. | 435/243 |
| 4,357,423 | 11/1982 | Cox et al. | 435/101 |
| 4,638,059 | 1/1987 | Sutherland | 536/121 |

FOREIGN PATENT DOCUMENTS 0102535 3/1984 European Pat. Off. ............ 435/105

OTHER PUBLICATIONS

Daggett et al., eds., *American Type Culture Collection Catalogue of Strains I*, 15th ed., (1982), p. 112.

Voelskow, "Production of Fucose by Hydrolysis of Polysaccharides Produced by Bacteria Including *Enterobacter sakazakii*"*Chem. Abst*, vol. 100, pp. 12–19 (Mar. 1, 1984) Abst. No. 173171t.

Nippon Starch Refining Co., Ltd. "Polysaccharides," *Chem. Abst.*, vol. 99, p. 5 (Feb. 8, 1983) Abst. Nos. 72486e, 72487f.

*Primary Examiner*—Elizabeth C. Weimar

[57] ABSTRACT

A novel heteropolysaccharide produced by strains of *Enterobacter sakazakii*, such as *Enterobacter sakazakii* ATCC 53017, *Enterobacter sakazakii* ATCC 29004, and *Enterobacter sakazakii* ATCC 12868, is disclosed. The heteropolysaccharide comprises from about 13 to about 22 percent by weight of L-fucose, from about 19 to about 24 percent by weight of D-galactose, from about 23 to about 30 percent by weight of D-glucose, from about 0 to about 8 percent by weight of D-mannose, from about 29 to about 32 percent by weight of glucuronic acid, said percent ranges based on total carbohydrate; the heteropolysaccharide further comprising about 1 to about 1.5 equivalents of ester per equivalent of neutral sugar. The heteropolysaccharide has many uses as a suspending, thickening, or stabilizing agent, and is particularly useful as a frictional drag reduction agent in aqueous systems.

11 Claims, 1 Drawing Sheet

HETEROPOLYSACCHARIDE PRODUCED BY *ENTEROBACTER SAKAZAKII*

BACKGROUND OF THE INVENTION

The ability of many microorganisms to produce extracellular polymers is well known. Of particular interest are some heteropolysaccharides because of their unique viscosity and rheology properties. Most notable among this group of polymers is xanthan gum which is produced by strains of the bacterial genus Xanthomonas. Xanthan gum has proven to be useful for a variety of applications. Examples include as a food additive (see U.S. Pat. Nos. 3,519,434; 3,557,016; 3,692,541; 3,726,690), as a stabilizing agent, friction reducing agent, or suspending agent in the petroleum industry (see U.S. Pat. Nos. 3,305,016; 3,319,715; 3,618,664), as a suspending agent for paints and starch (see U.S. Pat. Nos. 3,481,889; 3,692,552), and as a gelling agent for explosives, detergents, and sanitizers (see U.S. Pat. Nos. 3,326,733; 3,655,579; 3,741,805). These examples are only illustrative of the many uses of xanthan gum and are not meant to be exhaustive. Other uses can be found in the literature.

Other heteropolysaccharides produced by organisms other than Xanthomonas have been found to have properties and uses similar to that of xantham gum. U.S. Pat. No. 3,933,788 discloses a heteropolysaccharide produced by *Klebsiella pneumoniae* (originally classified as *Erwina tahitica*) and U.S. Pat. No. 4,329,448 discloses a heteropolysaccharide produced by *Bacillus polymyxa*.

The present invention discloses a novel heteropolysaccharide which can be produced by several known bacteria as well as a novel bacterium of the species *Enterobacter sakazakii*. The polymer of the present invention has unique viscoelastic properties and is superior to known heteropolysaccharides such as xanthan gum in its ability to reduce the frictional drag of fluids.

SUMMARY OF THE INVENTION

This invention relates to a novel polymeric heteropolysaccharide produced by an appropriate organism such as a strain of bacteria of the species *Enterobacter sakazakii*. As appreciated by one skilled in the art, the composition and molecular weight of the polymer will vary somewhat depending upon the particular strain of bacteria employed and the particular culture conditions. The heteropolysaccharide of this invention was initially found in tea and will hereinafter be referred to as the "tea polysaccharide."

The tea polysaccharide is comprised of about 23 to about 30% D-glucose, about 19 to about 24% D-galactose, about 13 to about 22% L-fucose, and about 29 to about 32% of glucuronic acid. D-mannose may also be present in the polymer in amounts up to about 8%. These percent ranges are based on weight percent of total carbohydrate. In addition, there is about 1 to about 1.5 equivalents of ester per equivalent of neutral sugar. Said ester typically comprises a carboxylic acid of at least eight carbon atoms. For the purpose of the present invention, the term "neutral sugar" refers to the neutral carbohydrates in the tea polysaccharide, that is, D-glucose, D-galactose, L-fucose, and D-mannose. Typically, the molecular weight of the polymer is at least 2,000,000 daltons.

This invention also relates to a process for producing the tea polysaccharide which comprises cultivating an appropriate organism in a medium containing suitable nutrients and recovering the tea polysaccharide therefrom. The tea polysaccharide is preferably produced by known appropriate strains of *Enterobacter sakazakii* such as *E. sakazakii* ATCC 29004 and *E. sakazakii* ATCC 12868. However, the most preferred production of tea polysaccharide is by a novel strain of *Enterobacter sakazakii* originally isolated from a portion of ordinary tea. A subculture of the novel *Enterobacter sakazakii* isolate has been made part of the permanent collection of the American Type Culture Collection, 12301 Parklawn Drive, Rockville, Md., where it is assigned the accession number 53017. This novel organism will hereinafter be referred to as *Enterobacter sakazakii* ATCC 53017. Mutants of this novel organism are considered within the scope of this invention. Mutants of the organism can be obtained by chemical and physical techniques or by other techniques known in the art. As used herein, the term "appropriate organism" or "appropriate strain" refers to an organism capable of producing tea polysaccharide upon growth or cultivation of said organism.

*Enterobacter sakazakii* is classified as a member of the family Enterobacteriacae. Other members of this family such as *Klebsiella pneumoniae* (orginally classified as *Erwina tahitica*) as described in U.S. Pat. No. 3,933,788 have been shown to produce heteropolysaccharide polymers. *Enterobacter sakazakii* has been cited many times in the open literature (e.g., Farmer et al., *International Journal of Systemic Bacteriology*, 30(3), pp. 569 to 584 (1980), hereinafter referred to as "Farmer"). In addition, West German patent application No. 3,300,633 teaches that Enterobacter or Klebsiella type bacteria, particularly *Enterobacter sakazakii* or *cloacae* or *Klebsiella pneumoniae* may produce a fucose-rich polysaccharide. However, the isolation and characterization of the tea polysaccharide and its desirable properties described herein have heretofore been unknown and unappreciated.

Because of its viscosity and rheology properties, the tea polysaccharide is useful in a variety of applications where a thickening, suspending, or stabilizing agent is desired. The polymer is particularly useful as a frictional drag reducing agent in aqueous systems. As used herein, the term "effective amount" refers to that amount of tea polysaccharide which reduces the frictional drag of a fluid below the frictional drag level of said fluid without the tea polysaccharide.

DETAILED DESCRIPTION OF THE INVENTION

Figure 1:
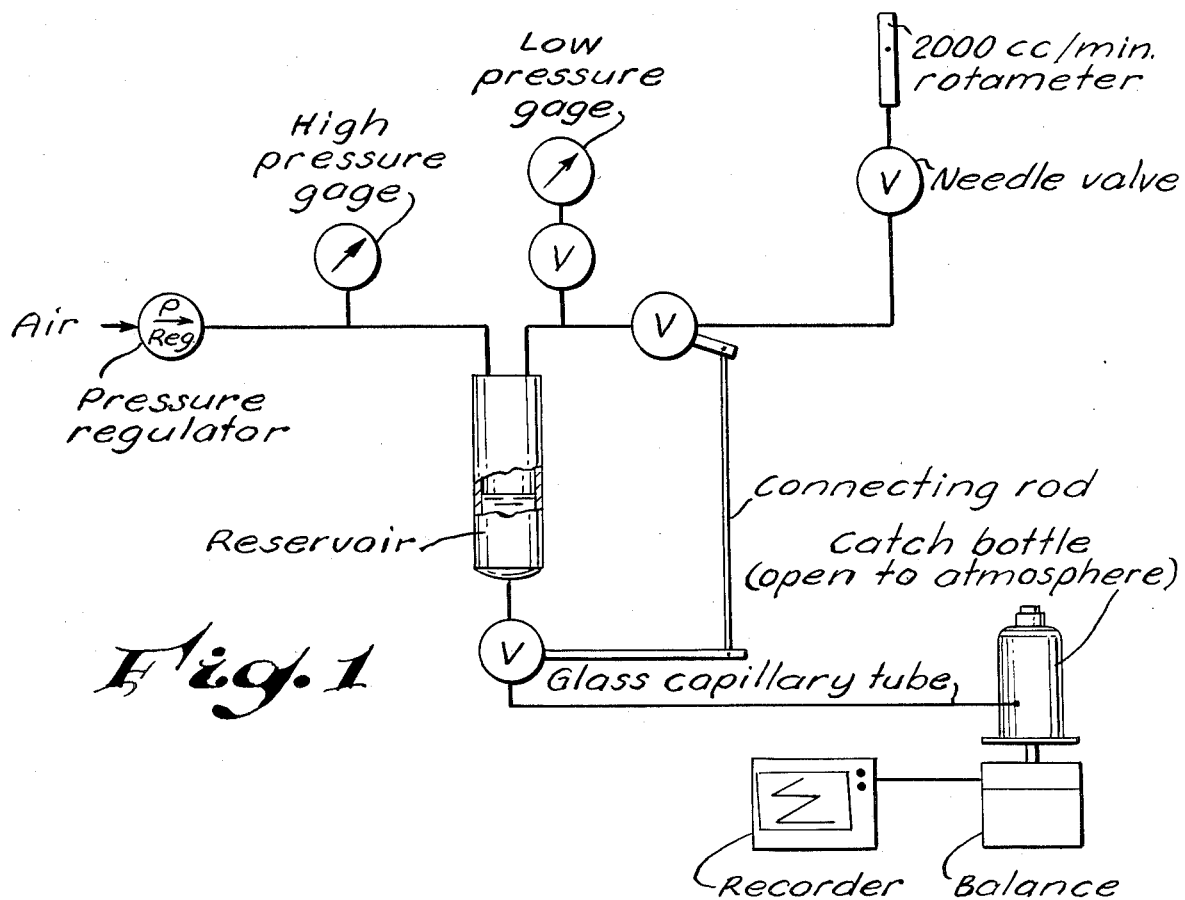
FIG. 1: A schematic diagram of the laboratory scale pipe flow friction reduction test apparatus used in Example 7. "cc/min" represents "cubic centimeters/minute".

*Enterobacter sakazakii* was first demonstrated to be a separate species by Farmer in 1980. The species had previously been known by various names such as the Urmenyi and Franklin bacillus, yellow pigmented *Enterobacter cloacae*, yellow coliform, pigmented *cloacae*

A organism, and yellow Enterobacter. According to Farmer, *Enterobacter sakazakii* is a gram negative rod about 3 micrometers (μm) long and 1 μm wide. The cells are motile by peritrichous flagella and do not form spores. Typical temperature growth range is about 25° C. to 45° C. The organism can grow both aerobically and anaerobically. The organism is capable of growing in conventional non-inhibitory media such as Trypticase Soy. Strains may produce a yellow pigment. Colonial morphology on agar media can vary from dry to mucoid. Biochemical reactions and carbohydrate utilization patterns of type strain *Enterobacter sakazakii* ATCC 29544 is described in Farmer. Tea polysaccharide can be produced by fermenting a culture medium comprising an appropriate strain of *Enterobacter sakazakii* or mutant thereof and suitable nutrients. Typically, the polymer is produced at a temperature range from about 20° C. to 40° C. Polymer production usually requires the presence of a conventional carbohydrate source in the medium such as glucose, sucrose, and the like. At least one of various organic and/or inorganic nitrogen sources are added to the medium such as yeast extract, tryptone, $NaNO_3$, or $NH_4Cl$. Essential trace elements and trace minerals necessary for growth of the organism and production of polymer can be added directly to the medium. Such trace elements and trace minerals commonly occur as impurities in the other constituents of the medium in amounts sufficient to meet the growth requirements of the organism. The pH range for growth of the organisms can vary considerably although good growth occurs between about pH 5 and about pH 9. After fermentation, the tea polysaccharide can be isolated from the medium by precipitation with a suitable water miscible solvent such as acetone, ethanol, or 2-propanol. When free of microbial cell debris, a 0.5% by weight aqueous solution of the polymer has a viscosity of about 500 centipoises (cps) as measured on a Haake Rotovisco viscometer, at a shear rate of 10.8 $sec^{-1}$, using an NV-cup and bob attachment at 2 revolutions per minute (RPM).

Although production of the tea polysaccharide by strains of *Enterobacter sakazakii* is preferred, the process of producing the tea polysaccharide by other appropriate organisms is also within the scope of the present invention. Such other appropriate organisms may inherently possess the ability to produce the tea polysaccharide upon growth or cultivation of said organisms. It is also possible that such other appropriate organisms may be capable of producing the tea polysaccharide as a result of genetic transformation or conjugation, or modification by plasmids or plasmid hydrids or phage or phage hydrids, or other vectors, each carrying deoxyribonucleic acid or ribonucleic acid specifying the synthesis of the tea polysaccharide.

The tea polysaccharide can be used in many of the applications for which known heteropolysaccharides are used. These include uses as a thickening, suspending, or stabilizing agent in aqueous systems. More specifically it is useful as an additive in foods such as salad dressings, puddings, bakery fillings, juice drinks, syrups and the like. The tea heteropolysaccharide is also useful as an additive in many industrial products such as pastes, adhesives, cleaners, gels, polishes, explosives, inks, paints, and the like. The tea polysaccharide is also useful as an additive in pharmaceutical compositions. Other uses of the tea polysaccharide are the same as those of heteropolysaccharide-10, and Biopolymer PS 87 disclosed in U.S. Pat. Nos. 3,933,788 and 4,329,448, respectively.

The tea polysaccharide irreversibly loses significant viscosity at high alkaline pH, e.g., above about pH 10. This property can be used advantageously in the drilling fluid field, in that high viscosity, although necessary at first to help suspend silts, is later detrimental in that the suspended solids must later be sedimented. This sedimentation is facilitated at low viscosity.

The tea polysaccharide shares some properties with xanthan gum such as pseudoplasticity. However, the tea polysaccharide differs from xanthan gum in other properties such as the former's viscoelasticity. This viscoelastic property is shared by another known heteropolysaccharide, i.e., okra mucilage. Okra mucilage is reputed to be a highly effective frictional drag reducing agent for potable water (R. L. Whistler and J. N. BeMiller, Industrial Gums, 2nd edition, Academic Press, New York, 1973, p. 361). The tea polysaccharide is superior to both xanthan gum and okra mucilage as a frictional drag reducing agent. An effective amount of the tea polysaccharide to reduce the frictional drag of a fluid is about 0.01% to about 2% by weight of the polymer in said fluid. Because of its frictional drag reduction properties, the tea polysaccharide is also useful for controlling the size of droplets in anti-misting applications.

Since it is a polysaccharide, preferred applications are where human contact or ingestion of the tea polysaccharide is possible. In addition to applications already mentioned, other uses include frictional drag reduction for irrigation or drinking water, spray drift control for herbicides and pesticides for food crops, spray drift control for forest fire fighting fluids, and the like.

In all of the hereinabove described applications, the tea polysaccharide is added in low concentration, i.e., from about 0.01% to about 2% by weight, using mixing and formulating techniques well known to those skilled in the particular art.

The present invention will be further illustrated with the following examples, however, these examples should not be interpreted as a limitation upon the scope of the present invention.

EXAMPLE 1

A novel strain of bacteria was isolated by conventional procedures known in the art from a portion of "solar brewed" tea which was kept at a warm temperature for several days. This organism produced an extracellular viscoelastic polymer which resulted in marked viscosity of the fermentation medium. The novel organism was determined to be a gram negative, nonsporeforming bacterium. The cells were motile with peritrichous flagella. After growth of the organism on the surface of an agar medium, yellow, leathery colonies with a rubber-like texture were produced which adhered to the medium. The yellow pigment was nondiffusible.

The novel organism was tested for reactions in standard biochemical and physiological tests, the results of which are shown in Table 1. The organism was also tested for its fermentation reactions with various carbohydrate sources, the results of which are in Table 2.

The properties of the novel organism were compared to those of known bacteria. The organism was determined to be a member of the family Enterobacteriacae because it is a facultative, gram negative, nonsporeforming rod which produces acid and gas from glucose. When all relevant characteristics including the biochemical reactions and carbohydrate reactions were considered, the novel organism was determined to be a strain of *Enterobacter sakazakii*. The characteristics of the novel strain of *E. sakazakii* was typical of the species *E. sakazakii* as described in Farmer. This novel organism is now known as *Enterbacter sakazakii* ATCC 53017.

TABLE 1
Biochemical and Physiological Properties of the Novel Organism

| Property | Result | Property | Result |
|---|---|---|---|
| Catalase | + | Potassium cyanide growth | + |
| Oxidase | − | Phenylalanine deamination | − |
| O—F glucose oxidative | + | Gluconate oxidation 37° C. | + |
| O—F glucose fermentative | + | Gluconate oxidation 26° C. | − |
| O—F glucose alkaline | − | Malonate as sole carbon source | − |
| MacConkey agar | + | Gelatinase | + |
| Indole | − | Nitrate to Nitrite | + |
| Methyl Red 37° C. | − | Pectin hydrolysis | − |
| Methyl Red 26° C. | − | Mucate utilization | − |
| Voges Proskauer 37° C. | + | Acetate as sole carbon source | + |
| Voges Proskauer 26° C. | − | Citrate utilization | + |
| Simmons Citrate | + | L-tartrate utilization | − |
| Lysine decarboxylase | − | Aesculin hydrolysis | + |
| Arginine (Mollers) | + | Tween 20 hydrolysis | + |
| Ornithine decarboxylase | + | Tween 80 hydrolysis | − |
| Hydrogen sulfide (TSI) | − | ONPG produced | + |
| Urease | − | | |

TABLE 2
Fermentation Properties of the Novel Organism Using Various Carbohydrate Sources

| Carbohydrate | Fermentation | |
|---|---|---|
| | Acid | Gas |
| adonitiol | − | − |
| L-arabinose | + | |
| cellobiose | + | − |
| D-glucose | + | + |
| dulcitol | − | |
| D-fructose | + | |
| glycerol | + | + |
| i-inositol | + | + |
| lactose | + | |
| maltose | + | |
| D-mannitol | + | |
| raffinose | + | |
| L-rhamnose | + | |
| salicin | + | |
| D-sorbitol | − | |
| sucrose | + | |
| trehalose | + | |
| D-xylose | + | |

EXAMPLE 2

A medium suitable for the growth of *Enterobacter sakazakii* and the production of the tea polysaccharide is a modification of Castenholtz Medium, ATCC No. 461 (hereinafter referred to as "modified Castenholtz medium"). The ingredients of modified Castenholtz medium are shown in Table 3.

TABLE 3
Ingredients of Modified Castenholtz Medium

| Growth Medium: Ingredients | Amount |
|---|---|
| ferric ammonium citrate | 0.02 g** |
| nitrilotriacetic acid | 0.04 g |
| *trace metal solution | 4.0 g |
| $CaCl_2$ | 0.20 g |
| KCl | 0.04 g |
| $MgSO_4$ | 0.40 g |
| $NaNO_3$ | 2.80 g |
| $NaHPO_4$ | 0.44 g |
| Yeast Extract | 4.0 g |
| Tryptone | 4.0 g |
| D-glucose | 100.0 g |
| distilled water | 1000.0 ml*** |
| final pH of medium = 7.2 | |

*Trace Metal Solution

| Ingredients | Amount |
|---|---|
| $Cu(NO_3)_2.6H_2O$ | 0.049 g |
| $ZnSO_4$ | 0.222 g |
| $MnCl_2.4H_2O$ | 1.81 g |
| $H_3BO_3$ | 2.86 g |
| $CuSO_4.5H_2O$ | 0.079 g |
| $NaMoO_4.2H_2O$ | 0.03 g |
| distilled water | 1000.0 ml |

**grams (g)
***milliliters (ml)

EXAMPLE 3

A pure culture of *Enterobacter sakazakii* ATCC 53017 was inoculated into sterile modified Castenholtz medium and incubated for 24 hours (hr). 7.5 ml of this seed culture was used to inoculate 150 ml of sterile modified Castenholtz medium in a 500 ml fermentation flask. The inoculated medium was incubated for 24 hrs at 30° C. in a gyrotory shaker. After fermentation, the medium was observed to be extremely viscous, almost gelled, and to exhibit viscoelasticity, i.e., tending to "snap back" when gently swirled.

EXAMPLE 4

The fermentation medium obtained from Example 3 was diluted with an equal volume of water and centrifuged at 20,000×gravity for at least one hour to remove cells and cell debris. The cleared supernatant solution was then decanted from the cell pellet into two volumes of acetone, in which a dense white, fibrous precipitate formed. This precipitate was collected, washed successively with 50% aqueous acetone and 100% acetone to yield, after drying, 280 milligrams (mg) solids. This precipitate was the tea polysaccharide.

EXAMPLE 5

Characterization of the Tea Polysaccharide 50 ml of water was added to 50 mg of the precipitate obtained from Example 4. This mixture was shaken for several hrs at 4° C. to dissolve the precipitate in the water. Aliquots of this polymer solution were analyzed for total carbohydrate (using the method described by M. Dubios, K. A. Gilles, J. K. Hamilton, P. A. Rebers, and F. Smith, *Anal. Chem.*, 28, pp 350–356 (1956)) by treatment with 1 ml of 5 percent phenol followed by 5 ml of concentrated (conc) $H_2SO_4$. The absorbance (490 nanometers (nm)) of the resulting test solution was determined using a Spectronic-21 (Spectronic is a trademark of Bausch & Lomb, Inc., Rochester, N.Y. 14601), and the results compared with those obtained using a 1 mg/ml glucose standard.

The stock polymer solution prepared above was analyzed for total ester (using the method described by Y. C. Lee, *J. Biol. Chem.*, 241, pp 1899–1908 (1966)) by treating known aliquots in the range of from 1 to 2 ml (diluted to 2 ml total volume) with 2M NH$_2$OH.HCl (0.4 ml) and 3.5M NaOH (0.4 ml) for 20 minutes (min), then with 4N HCl (0.4 ml) and 0.37M FeCl$_3$ in 0.1N HCl (0.4 ml). Absorbance (520 nm) was read after 5 min, and compared with that obtained from testing an ethyl acetate standard.

Total uronic acid content was determined (using the method described by N. Blumenkrantz and G. Asboe-Hansen, *Anal. Biochem.*, 54, pp 484–489 (1973)) by chilling known aliquots (typically the aliquot size was in the range of from 0.1 to 0.4 ml) of the stock polymer solution, adding 3 ml cold 0.0125M Na$_2$B$_4$O$_7$ in conc H$_2$SO$_4$, then heating in boiling water for 5 min., and adding 0.05 ml of 0.15% m-hydroxydiphenyl in 0.5% NaOH. Absorbance (520 nm) was compared with that obtained from testing a standard D-glucuronic acid solution.

Individual neutral sugars (i.e., D-glucose, D-galactose, L-fucose, D-mannose) were quantified by gas chromatography of their alditol acetate derivatives. A one milligram sample of the polymer was completely hydrolyzed in 2N trifluoroacetic acid. The hydrolysis mix was made slightly basic with 50% NaOH, and then 0.5 ml of 1% NaBH$_4$ in 0.1N NaOH was added. After at least 3 hrs at room temperature, this reduction reaction was quenched by the slow addition of glacial acetic acid, and then dried under a gentle stream of nitrogen. The residue was eluted through a 10 ml column of Dowex 50 (H+) (Dowex is a trademark of The Dow Chemical Company, Midland, Mich. 48640) to remove Na+, and then freeze-dried. The resulting fluffy, white residue was dissolved in methanol, then evaporated to dryness, and redissolved. This procedure was repeated three times to remove residual traces of borate. Pyridine and acetic anhydride (0.2 ml each) were then added to the residue, and the mixture heated at 90° C. for 15 min to acetylate the residue. The acetylation mixture was injected directly onto a 6 feet (ft)×2 millimeters (mm) glass column containing 3% OV-225 on Chromosorb WHP (Chromosorb is a trademark of the Johns-Manville Products Corporation, New York, N.Y. 10016). The alditol acetates were eluted isothermally at 200° C., and their retention times compared with those of standards. Quantitation was by an internal standard method, using the alditol acetate of arabinose as the internal standard.

The identity of the uronic acid residue on the polymer was established by reducing the acids on the intact polymer to their corresponding sugars, hydrolyzing the polymer, and determining the difference between the resulting monomer mix and that of the native polymer. Carboxyl-reduction (Taylor, Conrad, et al., *Biochem.*, 12(19), pp 3633–3637 (1973)) was performed on 10 ml of a 5 mg/ml solution of the polymer. One gram of 1-cyclohexyl-3-(2-morpholinoethyl)carbodiimide metho-p-toluene-sulfonate was added to the solution, and the pH adjusted to 4.75. This pH was maintained by pH-stat-addition of 0.1N HCl as the the reaction was allowed to run for 3 hrs, until there was no further requirement for HCl addition. NaBH$_4$ powder (2 gm) was then slowly added, and the mixture was agitated overnight at 55° C. The reduction was quenched with 4N HCl and the mixture dialyzed and freeze-dried. The carboxyl-reduction was then repeated as before to insure complete reaction. The resulting reduced polymer residue was hydrolyzed, derivatized, and analyzed by gas chromatography as described above, and the results compared with those of the native polymer to observe an increase in glucose content in the polymer on carboxyl-reduction. These results are indicative of the presence of glucuronic acid in the polymer.

From these data the carbohydrate composition of the tea polysaccharide produced as described herein was determined to be as shown in Table 4.

TABLE 4

Composition of the Tea Polysaccharide as Produced by *Enterobacter sakazakii* ATCC 53017.

| D-mannose | L-fucose | D-galactose | D-glucose | Glucuronic Acid |
|---|---|---|---|---|
| Weight Percent (Based on Carbohydrate Data): | | | | |
| 0 | 21.7 | 23.8 | 23.8 | 30.8 |
| Mole Percent (based on Carbohydrate data): | | | | |
| 0 | 29.4 | 29.4 | 29.4 | 11.8 |

In addition, it was determined that the tea polysaccharide produced by sstrain ATCC 53017 as described herein contains about 1.2 equivalents of ester per equivalent of neutral sugar. Said ester moiety comprised a carboxylic acid of at least eight carbon atoms.

EXAMPLE 6

The procedures described in Example 3 were substantially repeated for three known strains of *Enterobacter sakazakii*. These strains were *E. sakazakii* ATCC 29544, *E. sakazakii* ATCC 29004, and *E. sakazakii* ATCC 12868. Under these conditions, no significant amount of polymer was observed to be produced by strain ATCC 29544. However, strains ATCC 29004, and ATCC 12868 produced the tea polysaccharide which was substantially similar to that produced by *E. sakazakii* ATCC 53107. It is also believed that under other conditions that strain ATCC 29544 will also produce significant amounts of the tea polysaccharide. The tea polysaccharide produced by strain ATCC 29004 and strain ATCC 12868 were each respectively subjected to substantially the same isolation procedure and analyses as described in Example 4 and Example 5. The carbohydrate composition of the tea polysaccharide produced under these conditions was determined to be as shown in Table 5.

In addition, the tea polysaccharide as produced by strains ATCC 29004 and ATCC 12868 as described herein was determined to contain about 1.1 and about 1.3 equivalents, respectively, of ester per equivalent of neutral sugar.

Three strains of *E. sakazakii* (i.e., ATCC 53017, ATCC 29004, and ATCC 12868) have been shown to produce the tea polysaccharide. The minor variations in proportions of monosaccharides present in the polymer are consistent with the normal variations expected from different production runs. The exact composition of the tea polysaccharide will depend on, inter alia, the culture medium used, and culture conditions such as temperature, pH, and oxygen tension employed during a given fermentation run.

TABLE 5

Composition of the Tea Polysaccharide as Produced by
*Enterobacter sakazakii* ATCC 29004 and
*Enterobacter sakazakii* ATCC 12868

| Strain | D-mannose | L-fucose | D-galactose | D-glucose | Glucuronic Acid |
|---|---|---|---|---|---|
| Weight Percent (Based on Carbohydrate Data): | | | | | |
| ATCC 29004 | 7.1 | 16.2 | 19.5 | 26.6 | 30.6 |
| ATCC 12868 | 5.9 | 13.4 | 20.7 | 29.5 | 30.5 |
| Mole Percents (Based on Carbohydrate Data): | | | | | |
| ATCC 29004 | 9.1 | 22.7 | 25.0 | 34.1 | 9.1 |
| ATCC 12868 | 7.7 | 19.2 | 26.9 | 38.5 | 7.7 |

The results of the analyses performed on the tea polysaccharide demonstrate that the carbohydrate composition of the tea polysaccharide is within the following percentages by weight (based on carbohydrate data):

|  | Percent Weight |
|---|---|
| L-fucose | from about 13 to about 22 |
| D-galactose | from about 19 to about 24 |
| D-glucose | from about 23 to about 30 |
| D-mannose | from about 0 to about 8 |
| Glucuronic Acid | from about 29 to about 32 |

In addition to the carbohydrate composition, the tea polysaccharide also contains from about 1 to about 1.5 equivalents of ester per equivalent of neutral sugar. Said ester moiety typically comprises a carboxylic acid of at least eight carbon atoms.

The molecular weight of the tea polysaccharide was determined by using a Sephacryl S-500 column (Sephacryl is a trademark of Pharmacia, Inc., Piscataway, N.J. 08854) with a 0.1M ammonium acetate buffer at a flow rate of 0.7 ml/min with the refractive index as the detector. From the analysis it was determined that the molecular weight of the tea polysaccharide is at least 2,000,000 daltons.

EXAMPLE 7

The frictional drag reducing activity of the tea polysaccharide was evaluated in a laboratory scale pipe flow frictional drag reduction apparatus. The frictional drag reducing activities of xanthan gum and okra mucilage were also determined by the same apparatus and compared to the activity of the tea polysaccharide. The procedure is described as follows:

Equipment

A schematic of the equipment used for the test is shown in FIG. 1. Test fluid is added to the reservoir. Pressure is applied to the reservoir by a regulated air supply. A small air bleed is maintained during static conditions to simulate the flow conditions of the test while setting the pressure on the regulator. To initiate a test, the valve on the bottom of the reservoir is opened. Simultaneously the air bleed valve is closed by the linkage between the valves. While the test fluid flows through the capillary tube, the pressure is noted, and the flow rate is monitored by a recording balance.

Tea polysaccharide was added to water and the resulting solution was used as a test fluid. Similarly xanthan gum and okra mucilage were each independently added to water and each respective resulting solution was used as a test fluid. Water alone was also used as a test fluid.

The frictional drag reducing activity of each test fluid was determined by collecting several pressure/flow rate data points. These data points were used to calculate the Fanning Friction Factor (FFF) and Solvent Reynolds Number (Re) values. The Fanning Friction Factor and Solvent Reynolds Number are given by the relationships $$FFF = (\Delta PD/4L)/(\tfrac{1}{2}\rho V^2)$$

$$Re = DV\rho/\mu$$

where
- $\Delta P$ = pressure drop (gauge reading)
- $D$ = diameter of the tube
- $L$ = length of the tube
- $V$ = linear velocity of fluid (mass flow rate/capillary area)
- $\rho$ = density of the solvent
- $\mu$ = viscosity of the solvent.

Plots of the Fanning Friction Factor versus Solvent Reynolds Number for each test fluid were prepared and compared. Lower Fanning Friction Factors at the same Solvent Reynolds Numbers indicate that the solutes are providing frictional drag reduction. These plots provide a generalized way to compare data obtained in different equipment and they also can be used to predict drag reduction activity in other equipment.

Results

Figure 2:
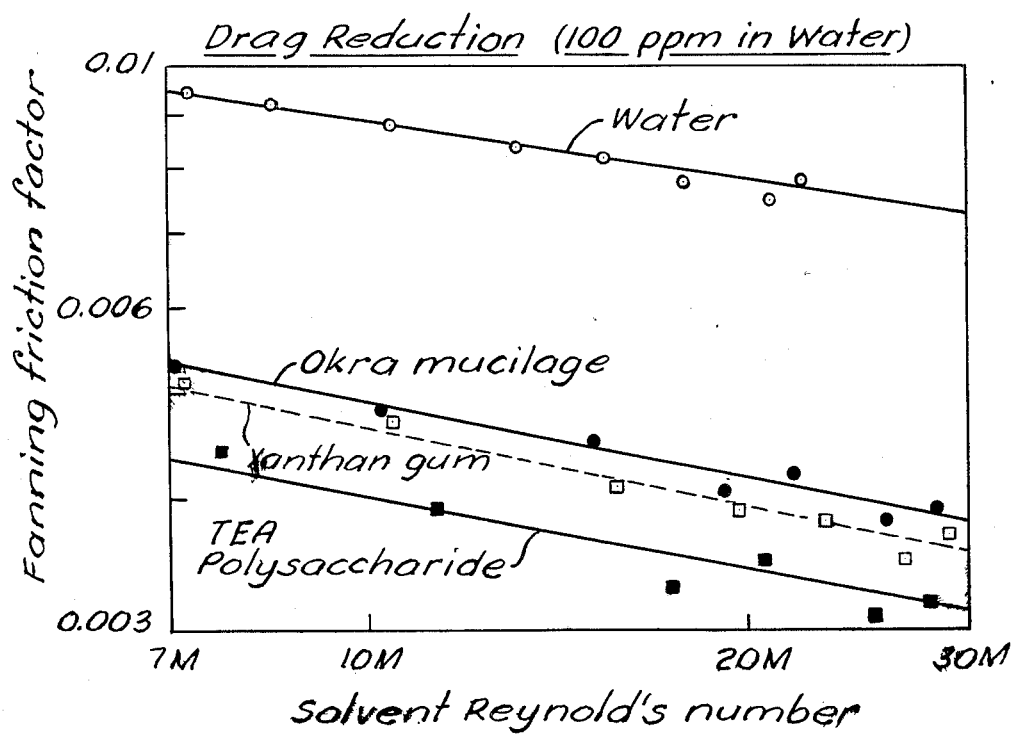
FIG. 2: Plot of the Fanning Friction Factor versus the Solvent Reynolds Number for the following: water (○); 100 parts per million (ppm) of okra mucilage in water (●); 100 ppm of xanthum gum in water ( ); and 100 ppm of the tea polysaccharide in water ( ). "M" on the abscissa represents "thousand".

The FFF versus Re data for a 100 parts per million (ppm) solution in water of the tea polysaccharide, xanthan gum, and okra mucilage, respectively, is shown in FIG. 2. Water is included as a control. Comparison of the data demonstrates that the tea polysacchacide gives the best frictional drag reduction of all polymers tested.

What is claimed is:

1. Tea polysaccharide, a heteropolysaccharide which comprises from about 13 to about 22% by weight of L-fucose, from about 19 to about 24% by weight of D-galactose, from about 23 to about 30% by weight of D-glucose, from about 0 to about 8% by weight of D-mannose, from about 29 to about 32% by weight of glucuronic acid, said percent ranges being based on total carbohydrate; said heteropolysaccharide further comprising about 1 to about 1.5 equivalents of ester per equivalent of neutral sugar.

2. The tea polysaccharide of claim 1 wherein the carbohydrate portion comprises about 21.7% by weight of L-fucose, about 23.8% by weight of D-galactose, about 23.8% by weight of D-glucose, and about 30.8% by weight of glucuronic acid; said tea polysaccharide further comprising about 1.2 equivalents of ester per equivalent of neutral sugar.

3. The tea polysaccharide of claim 1 wherein the carbohydrate portion comprises about 13.4% by weight of L-fucose, about 5.9% by weight of D-mannose, about 20.7% by weight of D-galactose, about 29.5% by weight of D-glucose, and 30.5% by weight of glucuronic acid; said tea polysaccharide further comprising about 1.3 equivalents of ester per equivalent of neutral sugar.

4. The tea polysaccharide of claim 1 wherein the carbohydrate portion comprises about 16.2% by weight of L-fucose, about 7.1% by weight of D-mannose, about 19.5% by weight of D-galactose, about 26.6% by weight of D-glucose, and about 30.6% by weight of glucuronic acid; said tea polysaccharide further comprising about 1.1 equivalents of ester per equivalent of neutral sugar.

5. The tea polysaccharide of claim 1 wherein said ester is comprised of a carboxylic acid of at least eight carbon atoms.

6. The tea polysaccharide of claim 1 wherein about a 5% aqueous solution of said tea polysaccharide has a viscosity of about 500 centipoises.

7. The tea polysaccharide of claim 1 wherein said tea polysaccharide has a molecular weight of at least 2,000,000 daltons.

8. A process for producing tea polysaccharide as described in claim 1 which comprises growing *Enterobacter sakazakii* ATCC 53017 or a mutant thereof, *Enterobacter sakazakii* ATCC 29004 or a mutant thereof, or *Enterobacter sakazakii* ATCC 12868 or a mutant thereof in a suitable growth medium at a pH of about 5 to about 9 and a temperature of about 20° C. to 40° C. at least until said tea polysaccharide is produced.

9. The process of claim 8 wherein said tea polysaccharide is recovered from the growth medium.

10. The process of claim 8 wherein said medium is modified Castenholtz medium.

11. A biologically pure culture of *Enterobacter sakazakii* ATCC 53017 which produces a recoverable amount of tea polysaccharide as defined in claim 1.

* * * * *